United States Patent [19]

Horrobin

[11] Patent Number: 5,324,748
[45] Date of Patent: Jun. 28, 1994

[54] METHOD FOR ENHANCEMENT OF 1-SERIES PG PRODUCTION

[75] Inventor: David F. Horrobin, Montreal, Canada

[73] Assignee: Efamol Limited, London, United Kingdom

[21] Appl. No.: 956,460

[22] Filed: Oct. 2, 1992

Related U.S. Application Data

[63] Continuation of Ser. No. 620,440, Nov. 30, 1990, abandoned, which is a continuation of Ser. No. 331,023, Mar. 28, 1989, abandoned, which is a continuation of Ser. No. 9,093, Jan. 29, 1987, abandoned, which is a continuation of Ser. No. 700,065, Feb. 11, 1985, abandoned, which is a continuation of Ser. No. 397,350, Jul. 12, 1982, abandoned.

[30] Foreign Application Priority Data

Jul. 14, 1981 [GB] United Kingdom ............... 81/21668

[51] Int. Cl.$^5$ ..................... A61K 31/20; A61K 31/07; A61K 31/015
[52] U.S. Cl. .................... 514/560; 514/559; 514/725; 514/763
[58] Field of Search .............. 514/560, 725, 763, 559

[56] References Cited

U.S. PATENT DOCUMENTS

| | | | |
|---|---|---|---|
| 3,962,416 | 6/1976 | Katzen | 424/493 |
| 4,273,763 | 6/1981 | Horrobin | 424/145 |
| 4,302,447 | 11/1981 | Horrobin | 424/145 |
| 4,309,415 | 1/1982 | Horrobin | 424/145 |
| 4,407,821 | 10/1983 | Mendy | 514/52 |
| 4,415,554 | 11/1983 | Horrobin | 424/145 |
| 4,444,755 | 4/1984 | Horrobin | 424/145 |

FOREIGN PATENT DOCUMENTS

| | | |
|---|---|---|
| 1117012 | of 1978 | Canada . |
| 1136044 | of 1979 | Canada . |
| 3407 | 8/1979 | European Pat. Off. . |
| 4770 | 10/1979 | European Pat. Off. . |
| 19423 | 11/1980 | European Pat. Off. . |
| 1082624 | 9/1967 | United Kingdom . |

OTHER PUBLICATIONS

Deper, Au Ludex of Tumor Chemotherapy, p. 10, 149 (1949).

Chemistry and Physics of Lipids, Michael E. Begin, Elsevier Scientific Publishers Ireland Ltd. pp. 269–313 (1987).

Booyens et al. S. African Medical J. 65 pp. 240–242 (Feb. 16, 1984).

Booyens et al. Med. Hypotheses 12, pp. 195–201 (1983).

Primary Examiner—Jerome D. Goldberg
Attorney, Agent, or Firm—Nixon & Vanderhye

[57] ABSTRACT

A composition of an effective amount of (a) γ-linolenic acid and/or dihomo-γ-linolenic acid, optionally in association with linoleic and if desired other fat acids, said acids being used if desired as physiologically functional derivatives thereof, in conjunction with (b) an effective amount of one or more of natural or synthetic carotenoids or retinoids having, or giving rise in the body to compounds having, Vitamin A activity when used in therapy of a condition in which enhancement of 1-series PG production, or more broadly influence of the 1-series/2-series PG balance in the body in favor of 1-series PGs is required.

2 Claims, No Drawings

METHOD FOR ENHANCEMENT OF 1-SERIES PG PRODUCTION

This is a continuation of application Ser. No. 07/620,440, filed Nov. 30, 1990, now abandoned, which is a continuation of application Ser. No. 07/331,023, filed Mar. 28, 1989, now abandoned, which in turn is a continuation of application Ser. No. 07/009,093, filed Jan. 29, 1987, now abandoned, which is a continuation of application Ser. No. 06/700,065, filed Feb. 11, 1985, now abandoned, which in turn is a continuation of application Ser. No. 06/397,350, field Jul. 12, 1982, now abandoned.

FIELD OF THE INVENTION

This invention relates to the treatment of certain diseases and disorders primarily, but not exclusively, in the field of human medicine and to compositions for use therein.

GENERAL BACKGROUND

Considerable interest has been shown in recent years in the use of prostaglandin (PG) precursors in medicine.

For various reasons it is not practical to administer naturally-occurring prostaglandins such as PGE 1 and PGE 2 to patients. Consequently, considerable attention has focussed on the use of prostaglandin precursors including linoleic acid, γ-linolenic acid (GLA) and dihomo-γ-linolenic acid (DGLA).

Conversion of these materials in the body is believed to be as shown in the following diagram:

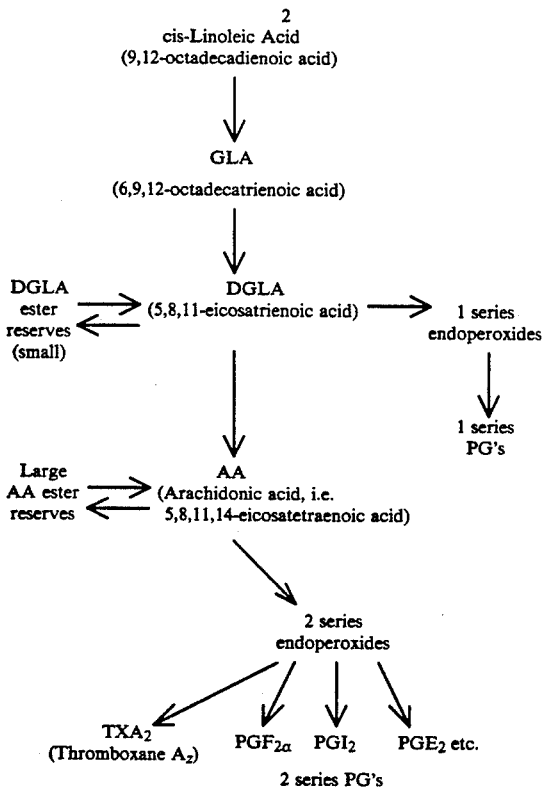

The broad outline of this pathway is well known, and it brings out clearly that a major function of essential fatty acids (EFAs) is to act as precursors for prostaglandins, 1-series PGs being formed from dihomo-γ-linolenic acid (DGLA) and 2-series PGs from arachidonic acid (AA). DGLA and AA are present in food in only small quantities, and the major EFA in food is linoleic acid which is first converted to γ-linolenic acid (GLA) and then to DGLA and AA. The conversion of linoleic acid to GLA is blocked by a high fat and high carbohydrate diet, by ageing and for example by diabetes. Stores of AA in the body in the form of lipid esters are very large indeed. In contrast only small amounts of DGLA ester are present.

INVENTION AND DETAILED BACKGROUND

DGLA is the key substance. GLA is almost completely and very rapidly converted in the body to DGLA and so for practical purposes the oral administration of DGLA and GLA amounts to the same thing. DGLA can be converted to a storage form, changed, to arachidonic acid and thence to PGs of the 2 series, or converted to PGs of the 1 series.

There is increasing evidence that PGs of the 1 series play a vital role in a number of key areas. First, PGE1 activates T lymphocytes. Defective T lymphocytes are believed to be involved in causing a wide range of allergic and inflammatory disorders and in making individuals susceptible to cancer and infections of all types. Second, PGE 1 is important in preventing over-production of collagen and fibrous tissue, a factor which plays a major role in arthritis and the so-called collagen diseases. Third, PGE 1 levels are extremely low in patients with schizophrenia and are moderately low in patients with depression. Fourth, PGE 1 appears to be important in controlling cholesterol levels and necessary for the normal actions of insulin. Fifth, PGE 1 dilates blood vessels and may be expected to be helpful in any situation in which vessel spasm occurs. Sixth, PGE 1 appears to inhibit the production of 2-series PG's, levels of which are raised in a wide variety of inflammatory disorders. Seventh, PGE 1 increases production of cyclic AMP which has anti-inflammatory effects.

There are therefore very strong reasons for influencing the 1-series/2-series PG balance in the body in favour of 1-series PG's and specifically for selectively enhancing formation of PGs of the 1-series and particularly PGE1. The diseases and disorders below are among those in which such action is indicated:

1. Defective T lymphocyte function including such defective function as allergic and inflammatory disorders, multiple sclerosis, schizophrenia and cancer.
2. Defective regulation of collagen formation and breakdown including such defective regulation as including rheumatoid arthritis, systemic lupus erythematosus, Crohn's disease and the "collagen" diseases.
3. Mental illnesses showing low PGE 1 levels including depression, schizophrenia and alcohol withdrawal and the latter stages of alcohol intoxication. In depression for example platelet PGE 1 production is moderately reduced whereas in schizophrenia it is severely reduced.
4. Disorders of lipid and carbohydrate metabolism including diabetes mellitus and disorders in which blood cholesterol levels are elevated.
5. Disorders in which blood vessels go into spasm including angina pectoris, myocardial infarction and Raynaud's syndrome; also hypertension.

6. Disorders of inflammation showing excessive production of 2-series PGs from arachidonic acid including disorders showing also low levels of cyclic AMP.

The present application is concerned with the treatment of malignant tumors which are sensitive to gamma-linolenic acid or dihomo-gamma-linolenic acid.

Selective enhancement of 1-series PG production has been explored in human platelets. The method is given in detail later herein but briefly human platelets are incubated with radioactive DGLA or arachidonic acid. The PGs produced during incubation are extracted by conventional means and separated by thin layer chromatography, and the amount of radioactivity appearing in each PG or related substance is counted. PGE 1, PGF 1α and thromboxane B1 from DGLA and PGE 2, PGF 2α and thromboxane B2 from AA are estimated. The results, as given herein, demonstrate the inventor's belief that the effects of various agents on AA and DGLA conversion can be quite different and that it is possible to selectively enhance formation of PGE 1 and other 1-series PG compounds. The effect is believed to be by influencing the conversion of DGLA to the 1-series PGs.

The balance between 1-series and 2-series PGs is, the inventor believes, significant in terms of overall control of the conversion pathways given earlier. Such control is not understood in detail but without restriction to the theory it appears first that PGE 2 is able to enhance the formation of 1-series PGs and second that PGE 1 is able to block arachidonic acid mobilisation from tissue stores. Thus the condition for a negative feedback control loop exists; overproduction of PGE 2 from AA will activate PGE 1 synthesis, the PGE 1 will inhibit AA mobilisation, and production of 2-series PGs will drop. Further, TXA 2, an unstable product of the 2-series endoperoxides arising in 2-series PG production, also appears to enhance 1-series PG and in particular PGE 1 production. Thus again the activity of the 2-series PG synthesis pathway gives rise indirectly to a material that controls that pathway.

EFFECTIVE AGENTS

The inventor proposes the following agents for their beneficial effect on PG metabolism, namely natural or synthetic carotenoids or retinoids having, or giving rise in the body to compounds having, Vitamin A activity, and in particular β-carotene, other various isomers of retinoic acid, retinal and retinols, and their Vitamin A active derivatives.

The structure of the retinol form of Vitamin A is, for example;

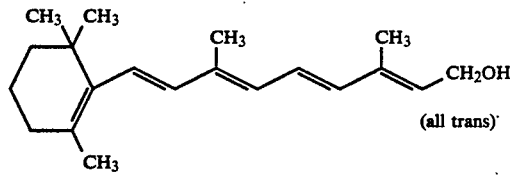

(all trans)

while β-carotene may be regarded as two such molecules joined by an ethylene group in place of the two —CH$_2$OH groups.

SPECIFIC RESULTS ON RETINOIC ACID

Retinoic acid, chosen as a type compound representative of retinoids in general, has been tested for effect on PG metabolism in the human platelet system, The technique is given in detail below. Using it, retinoic acid was incubated with platelets supplied with either 14C-AA or 14C-DGLA, control experiments being done without the retinoic acid. Results, with amounts expressed as percentages of the controls, were:

| Precursor acid<br>Product | DGLA<br>PGE1 | DGLA<br>TXB1 | AA<br>PGE2 | AA<br>TXB2 |
| --- | --- | --- | --- | --- |
| 1 μg/ml retinoic acid | 110% | 114% | 98% | 96% |
| 10 μg/ml retinoic acid | 118% | 121% | 81% | 77% |
| 100 μg/ml retinoic acid | 157% | 153% | 63% | 62% |

Similar tests on retinol 1 and retinal as other natural forms of Vitamin A have shown results of the same kind, enhancing DGLA conversion at concentrations which have no effect on AA conversion or actually reduce it.

MATERIALS AND METHODS

The detailed technique with platelets is given below by way of example.

(1-$^{14}$C) arachidonic acid and (1-$^{14}$C) dihomo-γ-linolenic acid were used, diluted with hexane to specific activities of about 5 μCi/μmol. One day expired (2 days old) human platelets were obtained and used within 48 hours of expiration. One unit was centrifuged at 1000 g for 15 minutes and the supernatant drawn off. The platelet pellet was resuspended in Tris-NaCl-EDTA buffer, made up of 0.15M NaCl, 0.15M Tris HCl at pH 7.4 and 0.077M NaEDTA (90:8:2 v/v/v). The platelets were recentrifuged, the supernatent removed and the pellet resuspended in Krebs-Henseleit buffer (without calcium) at pH 7.4. The washed platelet suspension contained about 1-2% red blood cells. All glassware used in the preparation of the platelets was siliconized.

Four equal sized 1 ml aliquots of the platelet suspension, containing $10^9$ platelets/ml were incubated with e.g. 0.5 μCi $^{14}$C-DGLA for five minutes. At the beginning of the incubation the material under test was added to the suspensions. The reaction was stopped after five minutes by addition of 1/10 volume of 10% formic acid. The suspension was then extracted three times with ethyl acetate and the fractions pooled and dried under vacuum. The extract was then taken up with 5 ml chloroform/methanol (2/1, v/v). Recovery of radioactive material in the extract was checked by taking 50 μl of the chloroform/methanol and counting by liquid scintillation. Recovery was in the range 80-95% in most experiments.

The chloroform/methanol extract was then reduced in volume to 1 ml under dry prepurified nitrogen. Thin layer chromatography was carried out on 500 μg precoated, prescored silica gel G Uniplates (Analtech). Plates were activated by heating to 100° C. for 1 hour immediately prior to use. The solvent system was chloroform:methanol:acetic acid:water (90:8:1:0.8). Reference compounds were run at the same time and visualised by phosphomolybdic acid spray followed by brief heating. The bands on the plates corresponding to the reference PGE1, PGF1α and TXB1 were scraped off and eluted with 20 ml acetone. Each elution was then evaporated to dryness and counted by liquid scintillation (Beckman 100 LS counter).

RELATIONSHIP TO PREVIOUS PROPOSALS

The above approaches may be used in combination with other materials as disclosed in the earlier patent applications of the inventor to which reference should be made, namely European Nos. 79/300079.5, 79/300546.3 and 80/301510.6 (Publication Nos. 0 003 407, 0 004 770 and 0 018 423; U.S. Ser. Nos. 004,924, 029,058 and 150,402.

Among these materials are a number believed to act by enhancing mobilisation of DGLA reserves, including zinc, penicillin and $\beta$-lactam antibiotics generally, and also penicillamine, phenformin and levamisole when the other effects of these materials are acceptable.

Further, since there is evidence that thromboxane A2 may indirectly enhance formation of PGE 1, substances such as colchicine, amantadine and melatonin, and also griseofulvin, vinblastine, vincristine and interferon as discussed in the patent specifications referred to above and believed to act through increasing the production or effect of thromboxane A2, can also be used in conjunction with the materials of the present invention.

In European Specification No.0019423 the further materials disclosed include Vitamin C, ethanol and opiate antagonists such as naloxone, again for this effect in PG metabolism.

As appears from the earlier patent specifications, in searching for ways to regulate PGE 1 formation the inventor has previously concentrated on the conversion of DGLA stores to free DLGA since this is believed to be a key rate-limiting step and since it has also been believed that factors which regulate conversion of free arachidonate to PGs will also regulate conversion of free DGLA to PGs. The present work has been more on the conversion of DGLA and of AA to the respective PGs, and as noted above it has been found that the factors regulating the two PG pathways are in some respects quite different. The discoveries on which the present application is based however build on and add to the earlier inventions rather than superseding them.

DETAILED STATEMENT OF THE PRESENT INVENTION

In the light of the general discussion above, and of the fact that compositions containing, inter alia, $\gamma$-linolenic acid and Vitamin A have been on sale in "health food" outlets as dietary supplements for purchase by the general public, the present invention in its various aspects may be summarised as:

A method of treating malignant tumors sensitive to $\gamma$-linolenic acid or dihomo-$\gamma$-linolenic acid in which a person suffering such tumor(s) is administered an effective amount of a synergistic mixture of: (a) $\gamma$-linolenic acid, dihomo-$\gamma$-linolenic acid or both or physiologically functional derivatives thereof in an amount of $\gamma$-linolenic acid of from 0.5 to 10 g daily or equivalent molar amount of said dihomo-$\gamma$-linolenic acid or derivative, or an amount of $\gamma$-linolenic acid and dihomo-$\gamma$-linolenic acid totalling from 0.5 to 10 g daily calculated on the weight of gamma-linolenic acid and molar amount of dihomo-$\gamma$-linolenic acid, in conjunction with (b) an effective amount of at least one natural or synthetic carotenoid or retinoid selected from the group consisting of retinol, retinoic acid and $\beta$-carotene, the amount of (b) administered being from 50 $\mu$ to 300 mg per day of retinol, from 1 mg to 3 g per day of retinoic acid, or from 1 mg to 6 g per day of $\beta$-carotene.

DOSE RANGES

Dose ranges in humans, initially individual doses, are for example as follows:

| | |
|---|---|
| Retinol | 50 $\mu$g to 300 mg/day preferably 3 to 15 mg/day |
| Retinoic acid | 1 mg to 3 g/day preferably 6 to 20 mg/day |
| $\beta$-Carotene | 1 mg to 6 g/day preferably 20 to 100 mg/day | and biologically equivalent amounts of the Vitamin A active materials described herein.

Dose ranges for materials auxiliary to those of the invention are discussed elsewhere herein. All the materials may be given in doses of for example one half, one third or one quarter of the above amounts. The amounts are related to those quoted earlier for platelet and other experiments, though of course a precise relation cannot be given in view of variation in inactivation and excretion rates and volume of distribution.

PACKS

If it is not desired to have compositions comprising the active materials together, as listed above, packs may be prepared comprising the materials presented for separate or part joint and part separate administration in the appropriate relative amounts, and use of such packs is within the purview of the invention.

DIETARY COMPOSITIONS

The invention is chiefly described in terms of pharmaceutical compositions, but it will be understood that the $\gamma$-linolenic and other acids, being in the nature of dietary supplements, could be incorporated in a dietary margarine or other foodstuffs; such foodstuffs, possibly containing other active materials and generally referred to in this description as dietary or pharmaceutical compositions, are within the purview of the invention and thus of the term pharmaceutical compositions, packs or the like used in the claims.

VETERINARY APPLICATIONS

It will be understood that where a disorder of a kind calling for treatment in animals arises, the invention while described primarily in terms of human medicine and treatment is equally applicable in the veterinary field.

AMOUNTS OF ACTIVE MATERIALS (ADJUNCTS TO PRESENT INVENTION)

Amounts of materials are:

| | |
|---|---|
| Zinc | 2.5 to 800 mg/day, preferably 10-80 mg calculated as zinc |
| $\beta$-lactam antibiotics | 0.5 to 10 g/day |
| Penicillamine | 50 mg to 10 g/day |
| Phenformin | 10 mg to 5 g/day |
| Levamisole | 10 mg to 2 g/day |
| Colchicine | 0.3 to 15 mg/day, preferably 0.6 to 2.4 |
| Melatonin | 10 mg to 5 g/day |
| Amantadine | 100 mg to 1000 mg/day |
| Griseofulvin | 0.5 to 5 g/day |
| Vinblastine | 0.5 to 5 mg/kg/week (average weight 70 kg) |
| Vincristine | 0.1 to 1.0 mg/kg/week |
| Interferon (by injection) | $1 \times 10^5$ to $1 \times 10^8$ units/day |
| Ascorbic acid | 50 mg to 50 g/day, preferably 250 mg to |

| | -continued |
|---|---|
| | 5 g/day |
| Naloxone | 0.1 to 500 mg/day, for example orally or parenterally in 4 or 6 divided doses, preferably 10 mg to 200 mg/day |
| Nalorphine | 1 mg to 5 g/day as last, preferably 10 mg to 2 g/day |
| Levallorphan | 0.2 mg to 1 g/day as last |
| Alcohol | 5 to 500 ml/day, preferably 50 to 200 ml/day |

All the materials may be given in doses of for example one half, one third or one quarter of the above amounts. The amounts are related to those quoted earlier for platelet and other experiments, though of course a precise relation cannot be given in view of variation in inactivation and excretion rates and volume of distribution.

Detailed discussion of suitable amounts and forms of use is contained in the published patent specifications referred to earlier, to which reference may be made. In particular the δ-lactam antibiotics are conveniently any of the known penicillin and cephalosporin antibiotics (including semi-synthetic antibiotics) such as, for exampla, penicillin G, penicillin N, penicillin V, cephalexin, cephalothin, ampicillin, amoxycillin, cloxacillin and cephaloglycin. Any of these may be used in the form of their physiologically functional non-toxic derivatives, for example alkali metal salts, e.g. sodium and potassium salts, and salts with organic bases, and reference to an antibiotic herein includes reference to such derivatives.

AMOUNT OF γ-LINOLENIC AND DIHOMO-γ-LINOLENIC ACIDS SPECIFICALLY

A preferred daily dosage for all purposes for an adult (weight ca 75 kg) is from 0.05 to 0.1 up to 1, 2, 5 or even 10 g as required derivative of either. Amounts in particular may be 0.1 to 1.0 g daily. Corresponding doses of the Oenothera oil containing 8 to 10% of γ-linolenic acid, are easily calculated. In place of, or in addition to, γ-linolenic acid, one may use dihomo-γ-linolenic acid or a physiologically functional derivative thereof, in amounts equivalent in molar terms to γ-linolenic acid and calculated as such. This dosage can for example be taken as a single dose or divided into 2, 3 or 4 subdivisions thereof as convenient.

FORMS AND SOURCES OF γ-LINOLENIC AND OTHER ACIDS

Convenient physiologically functional derivatives of γ-linolenic acid and dihomo-γ-linolenic acid for use according to the invention for all the purposes described include the $C_1-C_4$ alkyl (e.g. methyl) esters and the glycerides of the acids.

If desired, pharmaceutical compositions may be produced for use in the invention by associating natural or synthetic γ-linolenic acid (or a physiologically functional derivative thereof) and/or dihomo-γ-linolenic acid (or a physiologically functional derivative thereof), as such, with an acceptable pharmaceutical vehicle. It is at present convenient to incorporate the γ-linolenic acid into compositions in the form of an available oil having a high γ-linolenic acid content, hence references to "oil" herein.

At the present time known natural sources of oils having a high γ-linolenic acid content are few (there are no known natural sources of significant amounts of dihomo-γ-linolenic acid). One source of oils currently available is the seed of Evening Primrose species such as *Oenothera biennis L.* and *Oenothera lamarckiana*, the oil extract therefrom containing γ-linolenic acid (about 8%) and linoleic acid (about 72%) in the form of their glycerides together with other glycerides (percentages based on total fatty acids). Other sources of γ-linolenic acid are Borage species such as *Borago officinalis* which, though current yield per acre is low, provide a richer source of γ-linolenic acid than Oenothera oil. Recent studies on fungi which can be cultivated by fermentation promise a fungal oil source.

The seed oil extracts referred to above can be used as such or can for example if desired be fractionated to yield an oily composition containing the triglycerides of γ-linolenic and linoleic as the main fatty acid components, the γ-linolenic acid content being if desired a major proportion. Seed oil extracts appear to have a stabilising effect upon any dihomo-γ-linolenic acid or physiologically functional derivative thereof.

PHARMACEUTICAL PRESENTATION

The compositions according to the invention are conveniently in a form suitable for oral, rectal, parenteral or topical administration in a suitable pharmaceutical vehicle, as discussed in detail for example in Williams U.K. Patent Specification No. 1 082 624, to which reference may be made, and in any case very well known generally for any particular kind of preparation. Thus for example tablets, capsules, ingestible liquid or powder preparations, creams and lotions for topical application, or suppositories, can be prepared as required. Injectable solutions of hydrolysed Oenothera oil may be prepared using albumin to solubilise the free acid.

Advantageously a preservative is incorporated into the preparations. α-Tocopherol in a concentration of about 0.1% by weight has been found suitable for the purpose.

It will be understood that the absolute quantity of active ingredients present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired.

The following Examples serve to illustrate pharmaceutical compositions useful in treatment according to the invention:

EXAMPLES

Pharmaceutical compositions contain a unit dose of an oil extract from the seeds of *Oenothera biennis L.*, and of one of the active materials of the present invention, optionally with methyl dihomo-γ-linolenate and/or zinc oleate and/or penicillin V and/or any of the other active materials referred to herein directly or by cross reference to other patent applications of the inventor. They may be presented by encapsulation of the natural oil in soft gelatine capsules by known methods.

The oil is extracted from the seeds by one of the conventional methods of extraction such as cold pressure, screw pressure after partially cooking the seed, or solvent extraction.

Fractionation of a typical sample of this oil shows a yield of 97.0% oil in the form of methyl esters, with the relative proportions:

| | |
|---|---|
| Palmitate | 6.15 |
| Oleate | 10.15 |
| Linoleate | 72.6 |
| γ-Linolenate | 8.9 |

As preservative, α-tocopherol is added to the oil in a concentration of 0.1%.

Gelatin capsules containing oil extracts prepared as described above, each having the following contents of active ingredients (0.5 g oil extract=ca 0.045 g γ-linolenic acid), are prepared in conventional fashion.

The following are specific examples of capsules that may be given in treatment of the conditions listed earlier.

EXAMPLE 1

Capsules containing:
0.5 g Evening Primrose oil
3.0 mg Retinol
to be taken one capsule four times a day.

EXAMPLE 2

Capsules containing:
0.5 g Evening Primrose oil
1.0 mg Retinol
one capsule to be taken eight times a day Similarly, capsules containing the oil with 5 to 20 mg β-carotene or 1 to 5 mg of retinoic acid can be taken; or for example 1 to 3 mg of retinol or 1 to 5 mg of retinoic acid, can be taken in capsules otherwise as described in the Examples of the earlier patent specifications mentioned herein and containing for example in addition to the oil and carotenoid or retinoid 10 mg zinc sulphate or 0.25 g penicillin V (European Specification No. 0003407); or 0.15 to 0.3 mg colchicine, 100 mg amantadine, 25 mg lavamisole, 100 mg penicillamine, or the like (European Specification No. 0004770); or 200 mg ascorbic acid or 5 mg naloxone or the like (European Specification No. 0019423). Reference should be made to all other specifications for more details.

Further, topical preparations can be made, for example for use against acne, containing by weight from 0.01 to 0.1% of any of the active Vitamin A compounds, 0.1 to 25% Evening Primrose Oil, and base preparations to 100%.

I claim:

1. A method of treating malignant tumors sensitive to γ-linolenic acid or dihomo-γ-linolenic acid comprising administering to a person suffering therefrom an effective amount of a synergistic mixture of:

(a) γ-linolenic acid, dihomo-γ-linolenic acid or both or physiologically functional derivatives thereof in an amount of γ-linolenic acid of from 0.5 to 10 g daily or equivalent molar amount of said dihomo-γ-linolenic acid or derivative, or an amount of γ-linolenic acid and dihomo-γ-linolenic acid totalling from 0.5 to 10 g daily calculated on the weight of gamma-linolenic acid and molar amount of dihomo-γ-linolenic acid in conjunction with (b) an effective amount of at least one natural or synthetic carotenoid or retinoid selected from the group consisting of retinol, retinoic acid and β-carotene, the amount of (b) administered being from 50 μ to 300 mg per day of retinol, from 1 mg to 3 g per day of retinoic acid, or from 1 mg to 6 g per day of β-carotene.

2. The method as claimed in claim 1, wherein the amounts of (b) are:

| | |
|---|---|
| retinol | 3 to 15 mg per day |
| retinoic acid | 6 to 20 mg per day |
| β-carotene | 20 to 100 mg per day. |

* * * * *